United States Patent
Bombardelli et al.

(10) Patent No.: US 11,311,594 B2
(45) Date of Patent: Apr. 26, 2022

(54) **EXTRACTS OF *CYNARA CARDUNCULUS* AND *CITRUS AURANTIUM BERGAMIA*, COMBINATIONS THEREOF, AND FORMULATIONS CONTAINING THEM**

(71) Applicant: HERBAL E ANTIOXIDANT DERIVATIVES S.R.L. ED IN FORMA ABBREVIATA H&AD S.R.L., Bianco (IT)

(72) Inventors: Ezio Bombardelli, Gropello Cairoli (IT); Vincenzo Mollace, Bianco (IT)

(73) Assignee: Herbal & Antioxident Derivatives, S.R.L., Bianco (IT)

( * ) Notice: Subject to any disclaimer, the term of this patent is extended or adjusted under 35 U.S.C. 154(b) by 0 days.

(21) Appl. No.: 16/603,525

(22) PCT Filed: Apr. 10, 2018

(86) PCT No.: PCT/IB2018/052498
§ 371 (c)(1),
(2) Date: Oct. 7, 2019

(87) PCT Pub. No.: WO2018/189672
PCT Pub. Date: Oct. 18, 2018

(65) Prior Publication Data
US 2020/0384054 A1 Dec. 10, 2020

(30) Foreign Application Priority Data
Apr. 12, 2017 (IT) .................. 102017000040866

(51) Int. Cl.
| | | |
|---|---|---|
| A61K 36/00 | (2006.01) | |
| A61K 36/752 | (2006.01) | |
| A61K 31/7048 | (2006.01) | |
| A61K 36/28 | (2006.01) | |
| A61K 9/20 | (2006.01) | |
| A61K 9/48 | (2006.01) | |
| A61K 45/06 | (2006.01) | |

(52) U.S. Cl.
CPC ........ *A61K 36/752* (2013.01); *A61K 31/7048* (2013.01); *A61K 36/28* (2013.01); *A61K 9/20* (2013.01); *A61K 9/48* (2013.01); *A61K 45/06* (2013.01); *A61K 2236/31* (2013.01); *A61K 2236/331* (2013.01)

(58) Field of Classification Search
CPC .................................................. A61K 36/00
USPC ........................................................ 424/725
See application file for complete search history.

(56) References Cited

U.S. PATENT DOCUMENTS
8,741,362 B2   6/2014  Lombardo et al.
2015/0231193 A1   8/2015  Bombardelli et al.

FOREIGN PATENT DOCUMENTS
| EP | 2719287 A1 | 4/2014 |
| WO | 2008105023 A1 | 9/2008 |
| WO | 2008142460 A2 | 11/2008 |
| WO | 2015136441 A1 | 9/2015 |

OTHER PUBLICATIONS

Invasive Species Compendium, 1-5, 2020.*
Ammar et al., ISRN Agronomy, vol. 2104, Morphological Variability of Wild Cardoon (*Cynara cardunculus* L. var. *sylvestris*) Populations in North of Tunisia, Article ID 656937, 9 pages, 2014.*
De Cássia Gomes Rocha et al., Powder Technology, 343, 2019, 317-325.*
Elsbai et al., frontiers in pharmacology, Dec. 2016.*
Ferro A M et al., "Haplotype analysis of the germacrene A synthase gene and association with cynaropicrin content and biological activities in Cynara cardunculus", Molecular Genetics and Genomics, vol. 293, No. 2, Nov. 16, 2017, pp. 417-433.
Fragopoulou E. et al., "Mediterranean wild plants reduce postprandial platelet aggregation in patients with metabolic syndrome", Metabolism, Clinical and Experimental, vol. 61, No. 3, Jul. 13, 2011, pp. 325-334.
Mollace V, et al., "Hypolipemic and hypoglycaemic activity of bergamot polyphenols: from animal models to human studies", Fitoterapia, vol. 82, No. 3, 2011, pp. 309-316.
Rondanelli M., et al., "MediterrAsian diet products that could raise HDL-cholesterol: A systematic review", Biomed Research International, 2016, pp. 1-15.
Rondanelli M., et al., "Metabolic management in overweight subjects with naive impaired fasting glycaemia by means of a highly standardized extract from Cynara scolymus: A double blind, placebo-controlled, randomized clinical trial", Phytotherapy Research, Feb. 1, 2013, pp. n/a-n/a.
Search Report and Written Opinion of PCT/IB2018/052498 dated Sep. 27, 2018.

* cited by examiner

*Primary Examiner* — Michael V Meller
(74) *Attorney, Agent, or Firm* — Pharmaceutical Patent Atty's, LLC

(57) ABSTRACT

Disclosed is a combination of extracts of *Cynara cardunculus* and *Citrus bergamia* which are useful for the prevention and treatment of hepatic steatosis and other disorders correlated with dyslipidaemic conditions.

7 Claims, No Drawings

EXTRACTS OF *CYNARA CARDUNCULUS* AND *CITRUS AURANTIUM BERGAMIA*, COMBINATIONS THEREOF, AND FORMULATIONS CONTAINING THEM

This application is a U.S. national stage of PCT/IB2018/052498 filed on 10 Apr. 2018, which claims priority to and the benefit of Italian Application No. 102017000040866 filed on 12 Apr. 2017, the contents of which are incorporated herein by reference in their entireties.

The present invention relates to a combination of extracts of *Cynara cardunculus* and *Citrus bergamia* which are useful for the prevention and treatment of hepatic steatosis.

PRIOR ART

The bergamot orange (*Citrus bergamia* Risso & Poiteau) is a citrus fruit substantially cultivated only in small areas of Calabria, Italy. Three main varieties thereof are known, called Femminello, Fantastico and Castagnaro.

It has long been known that the bergamot orange represents a niche product of particular prestige in the Calabrian citrus fruit industry. Said citrus fruit develops in a limited area of the Province of Reggio Calabria. To date, bergamot orange has been used solely for the properties of its essential oil, which is in particular demand in the perfume industry because it has an exclusive fragrance that is still used as a base to prepare many perfumes by the best-known perfume manufacturers, and for the manufacture of eau de cologne. Said oil is obtained by peeling from the outermost portion (cuticle) of bergamot orange peel.

The bergamot orange is also known to possess significant antiseptic properties, and a derivative of bergamot orange, called Bergamon, has been manufactured and used as a disinfectant in operating theatres for many years.

Moreover, the relaxing properties of bergamot orange extracts, and its important nutraceutical properties, are known from traditional medicine.

Finally, the water-alcohol solution of bergamot orange essence is used to prepare some products (Bergarytal®) manufactured in the form of sprays which have a skin decongestant action, and are particularly effective as a mosquito repellent.

However, the identification of the potentially toxic action of some ingredients of bergamot orange essence, such as bergaptene, has limited its use, since procedures for removing said compound are required to ensure safe use of the essential oil extracts.

Bergamot orange juice, which is rich in polyphenols and flavonoids (brutieridin and melitidin), is also known to possess cholesterol-lowering and blood glucose-lowering activities (Vincenzo Mollace et al., *Hypolipemic and hypoglycaemic activity of bergamot polyphenols: From animal models to human studies*, Fitoterapia, vol. 82, no. 3, 2011, pp. 309-316).

U.S. Pat. No. 8,741,362 describes a plant extract obtained from the pith and juice of fresh fruit of *Citrus aurantium* var. *bergamia*, and a process for its preparation. Said plant compound, in the form of a dried extract, contains the polyphenols neoeriocitrin, naringin and neohesperidin in the amounts of 29.6±6.0, 32.4±4.0 and 38.0±6% respectively of their total, the flavonoids eriocitrin, neoeriocitrin, melitidin and brutieridin and polymerisation compounds of said flavonoids, and is substantially devoid of furocoumarins and coumarins, allergenic compounds which can have adverse effects on coagulation and the blood count.

The plant compound described in U.S. Pat. No. 8,741,362 normalises the lipid and blood glucose parameters in patients suffering from diet-dependent metabolic disorders or inherited genetic disorders. In pathological hyperlipaemia, a reduction in total cholesterol and LDL cholesterol to concentrations ranging from 20 to 32% has been demonstrated, with a 30% increase in HDL cholesterol. These important variations are associated with a marked reduction in VLDL cholesterol and a dimensional increase in LDLs, leading to a reduction in their oxidation. Bergamot orange extract has also improved the endothelial function, with vascular protection attributable to flavonoids. In double-blind clinical trials, the active dose reported is 650 mg at least twice a day.

The choleretic, cholagogic, hypoglycaemic, antidyspeptic and mildly hypocholesterolaemic action of artichoke (*Cynara scolymus*) extracts is also known. However the cholesterol reduction reported in numerous clinical trials is modest, never exceeding 10%. The published clinical trials report modest, erratic increases in HDL cholesterol following administration of high doses of *Cynara scolymus* extracts, amounting to several grams a day (Naturmed, 13, 17-24, 1998; Arzneim Forschung, 50, 260-65, 2000; The Cochrane Library, 2002, Issue 3). Standardised artichoke extracts containing 25% by weight of caffeoylquinic acids, 8% by weight of flavonoids and 7% by weight of cynaropicrin, which possess improved hypolipidaemic and hypoglycaemic activities, have been developed in recent years (Rondanelli et al., Phytotherapy Research 28:33-41 (2014) and Italian Journal of Medicine 2014; Vol 8, suppl 2, p. 113). Said extracts only exhibit a reasonable level of activity if administered twice a day, and in any event have little effect on major hyperlipidaemia.

The choleretic, hypoglycaemic and liver-protecting activity of artichoke extracts is attributed to caffeoylquinic acids, while flavonoids perform a hypolipidaemic action associated with cholesterol synthesis, and cynaropicrin exerts an anti-inflammatory and anti-STAT 3 action. *Cynara scolymus* extracts deprived of cynaropicrin, such as those prepared from non-bitter flower heads, have no effect on cholesterol, only on blood glucose.

The cardoon (*Cynara cardunculus* L.) is a species of plant belonging to the Asteraceae family. The variety *sylvestris* Lam. (wild cardoon) grows wild in profusion in the western Mediterranean basin.

WO 2008142460 discloses an anti-diabetic formulation comprising *Cynara cardunculus*, lemon balm, nettle, chicory and centaury extracts.

WO2014447533 discloses formulations for the treatment of metabolic syndrome comprising extracts of *Cynara scolymus* and *Olea europea*. The cynaropicrin content of *Cynara scolymus* extract is 10-18% by weight.

WO 2016136441 discloses a plant compound consisting of *Citrus bergamia* Risso et Poiteau and *Cynara scolymus* L. extracts, optionally associated with phytosterols and ascorbic acid, which is useful for the treatment of dyslipidaemia. The active ingredients of artichoke (*Cynara scolymus*) extract include chlorogenic acids and luteolin, but not cynaropicrin, only low percentages of which are contained in artichoke extract.

DESCRIPTION OF THE INVENTION

It has now been found that by simultaneously atomising aqueous solutions of the plant compound obtained according to U.S. Pat. No. 8,741,362 and a *Cynara cardunculus* leaf extract obtained from fresh biomass subjected to thermal shock, a composite extract is obtained which exhibits not only a synergic increase in the properties of the single extracts, but also an unexpected preventive and therapeutic activity towards hepatic steatosis.

The step of atomisation of the mixture of the solutions leads to an unexpected increase in the solubility of the ingredients of the extracts.

It has also been found that *Cynara cardunculus* extract, and in particular *Cynara cardunculus* var. *sylvestris* extract, has a much higher cynaropicrin content than *Cynara scolymus* extracts. The high cynaropicrin content (up to 40% by weight of the *Cynara cardunculus* var. *sylvestris* extract, exceeding not only that of *C. scolymus* but also those of other varieties of *cardunculus*) gives rise to an increase in therapeutic efficacy against various disorders, as described in more detail below.

It has also surprisingly been found that *Cynara cardunculus* extract, and especially *Cynara cardunculus* var. *sylvestris* extract, contains catechin polymers which enhance the beneficial effects of the extract.

A first aspect of the invention therefore relates to a composite extract obtained by atomising a mixture of a *Cynara cardunculus* extract, preferably a *Cynara cardunculus* var. *sylvestris* extract, and an aqueous extract of *Citrus bergami*, wherein the *Cynara cardunculus* extract is obtained by extraction with water of fresh leaves previously subjected to thermal shock, wherein the *Citrus bergami* extract has at least a 25% content by weight of a polyphenol fraction consisting of neoeriocitrin, naringin and neohesperidin, and a furocoumarin content of less than 400 mg/Kg.

A second aspect of the invention relates to pharmaceutical or nutraceutical formulations comprising the composite extract as defined above, mixed with suitable carriers and excipients.

The invention also relates to said formulations for use in the treatment and prevention of hepatic steatosis and in the treatment of dyslipidaemia, hyperglycaemia, vascular inflammation, hypertension, metabolic syndrome, type 2 diabetes, chemotherapy-induced heart disease, and cardiovascular disease.

The formulations of the invention have also proved useful to stimulate the stem cells of the myocardium, for the treatment of liver cancer and, in general, for the treatment of tumours by inhibiting the STAT-3 pathway.

A further aspect of the invention is an extract of *Cynara cardunculus* var. *sylvestris* leaves having a cynaropicrin content ranging from 20 to 40% by weight, a cynaroside content ranging from 5 to 30% by weight, and a catechin polymer content ranging from 5 to 10% by weight.

Finally, the invention relates to a process for the preparation of the composite extract as defined above, which comprises atomisation of a mixture of a *Cynara cardunculus* extract obtained by extraction with water of the fresh leaves, previously subjected to thermal shock, and an aqueous extract of *Citrus bergami*.

DETAILED DESCRIPTION OF THE INVENTION

The composite extract of the invention is obtained by atomisation or other equivalent techniques of aqueous solutions of:

a) a *Cynara cardunculus* extract having a cynaropicrin content ranging from 20 to 40%, and preferably amounting to 30% by weight;

b) a *Citrus aurantium* var. *bergamia* extract obtained by the steps described in the process according to U.S. Pat. No. 8,741,362, except for the pre-drying step.

The polyphenol ingredients most representative of bergamot orange extract are neoeriocitrin, naringin and neohesperidin, in the following percentages of the total weight of the three compounds:

Neoeriocitrin 29.6%±6.0
Naringin 32.4%±4.0
Neohesperidin 38.0%±6.0
Total 100.0%

The *Cynara cardunculus* extract is obtained by collecting the leaf mass when it reaches a height of about 40 cm. The biomass is then coarsely chopped in a steam current to inhibit hydrolytic enzymes and oxidants, then pressed after thermal shock at pressures ranging from 100 to 300 bars, preferably 200 bars. After pressing and counterwashes with water in countercurrent, the aqueous extract is centrifuged and filtered, and the clear filtrate is mainly treated with SEPABEADS SP absorption resin or other polystyrene resins; the resin, which retains the polyphenol substances, is washed thoroughly with water to remove inert substances, then eluted with ethanol or an ethanol/water mixture. The eluate is concentrated by evaporating the ethanol. The concentrate, after optional titration of the active ingredients, is added to the *Citrus bergamia* extract. The mixture is then concentrated until dry in a vacuum.

The resulting extract is formulated in forms suitable for oral administration, for example as conventional or gastro-protected capsules or tablets, sugar-coated pills, soft or hard gelatin capsules, or cellulose capsules.

The compositions of the invention will be formulated according to conventional methods, such as those described in "Remington's Pharmaceutical Handbook", Mack Publishing Co., N.Y., USA. In particular, the compositions of the invention will be formulated according to conventional plant ingredient formulation techniques, which require particular care to be taken to avoid interactions with the excipients and the capsule matrices.

Particularly suitable carriers are oils rich in co-3 fatty acids, which facilitate the absorption of cynaropicrin and flavonoids.

The formulations can also contain other active ingredients with complementary or otherwise useful activities, in particular one or more extracts of *Olea europaea, Berberis aristata, Olea oleracea, Vitis vinifera, Cyclanthera pedata, Gymnema sylvestre, Eugenia jambolana* and carotenoids.

The combination with the *Olea europaea* extract containing 20% oleuropein is particularly preferred. The release of tyrosol and hydroxytyrosol from oleuropein generates a reduction in oxidative processes affecting the cLDLs, which acts synergically with the properties of the combined artichoke and bergamot orange extracts.

The combination with the *Olea europaea* extract therefore maintains its therapeutic efficacy in the treatment of metabolic syndrome, even at low doses of the formulations according to the invention. Said combination, in addition to the primary activity against hepatic steatosis and lipid metabolism, acts on the blood pressure, adipose tissue and vascular inflammation. The growing adipose tissue is infiltrated by macrophages that release proinflammatory cytokines and inflammation mediators such as COX-2 and iNOS; moreover, the circulating fatty acids act as messengers of the adipose cells via the TLR-4 receptors, which induce the expression of inflammatory mediators by activating NF-kB or JNK. This cascade of events generates a state called "silent inflammation", whose aggressive action against the vascular endothelia causes lesions that act as the site of attack by atheromatous plaque, which is mainly responsible for the atherosclerotic and thrombotic symptoms that form the basis of cardiovascular disease. The *Olea europea* extracts contain substances useful to counteract the inflammatory process such as triterpenes, ursolic and oleanolic acids, flavonoids such as verbascoside, and the above-mentioned oleuropein. Hydroxytyrosol, released by oleuropein, has obtained a favourable opinion from the EFSA regarding the claim that it inhibits LDL oxidation, one of the secondary phenomena that induce the formation of atheromatous plaque.

The dose of the composite extract of the invention typically ranges from 400 to 200 mg/dose/day, preferably 300 mg/dose/day, a dose interval much smaller than those reported for the uncombined extracts (1.3 g for bergamot orange extract and 500 mg/day for artichoke extract).

The activity of the composite extract of the invention was evaluated in normal rats, obese Zucker rats and diabetic Zucker rats (ZDF) by comparison with the individual ingredients, extract of *Citrus bergamia* (BPF) and *Cynara cardunculus* (CC). The treatment was given for 30 days, and the metabolic state, insulin sensitivity, glucose tolerability and hepatic steatosis were evaluated. All the substances tested improved the parameters examined, but with a different intensity from the controls.

During euglycaemic treatment, hyperinsulinaemic treatment and treatment with BPF, CC and BCS, the Zucker rats and the diabetic Zucker rats required a higher glucose infusion than the controls to maintain a stable glucose concentration (1.6±0.23, 1.5±0.18, 2.01±0.19 and 4.1%, 1 and 6.42±1.03 mg min$^{-1}$) as against values compared with the controls (0.71±0.17 mg min$^{-1}$ and 2.09±0.71 p<0.05), demonstrating increased insulin sensitivity in both the Zucker rats and the diabetic Zucker rats.

The composite extract of the invention underwent a clinical trial at the dose of 300 mg once a day. The trial involved a total of 86 patients suffering from stable hyperlipaemia (fasting LDL values exceeding 130 mg/dl, triglycerides exceeding 200 mg/dl and HDL lower than 40 mg/dl), with an alcohol intake not exceeding 20 g a day and a fatty liver determined by abdominal ultrasound scan with a hepatorenal index ranging from 2.5 to 3.5 according to the conventional international criteria.

The duration of the clinical trial was 16 weeks, with tests conducted at time zero and at the end of the treatment. The results, set out in tables 1 and 2, demonstrate a synergic effect of the composite extract compared with the two individual extracts on the lipid and glycometabolic parameters, and on the liver parameters correlated with non-alcoholic hepatic steatosis.

TABLE 1

| Substances | Dose | CT | cLDL | cHDL | TG | oxLDL |
|---|---|---|---|---|---|---|
| BPF | 1300 | 241 ± 11 | 169 ± 18 | 35 ± 4 | 251 ± 8 | 131 ± 14 |
| | | Δ 16 − 50 ± 8 | Δ 16 − 40 ± 4 | Δ 16 13 ± 2 | Δ 16 − 46 ± 6 | Δ −18 ± 6 |
| *CYNARA C.* | 200 | 246 ± 9 | 165 ± 12 | 39 ± 2 | 239 ± 7.5 | 127 ± 4 |
| | | Δ −28 ± 6 | Δ −20 ± 8 | Δ 12 ± 4 | Δ −31 ± 6 | Δ −11 ± 3 |
| COMB. ES. 3 | 300 | 252 ± 10 | 172 ± 16 | 38 ± 3 | 210 ± 6 | 128 ± 4 |
| | | Δ −76 ± 9 | Δ −39 ± 5 | Δ 21 ± 4 | Δ −34 ± 2 | Δ −26 ± 2 |
| PLACEBO | | 251 ± 12 | 155 ± 8 | 39 ± 3 | 136 ± 14 | 129 ± 6 |
| | | Δ −6 ± 2 | Δ −6 ± 15 | Δ 5 ± 2 | Δ −10 ± 4 | Δ 4 ± 1 |

TC mg/dL, total cholesterol;
TG mg/dL triglycerides;
LDL-c mg/dL low-density lipoprotein;
HDL-c mg/dL high-density lipoprotein oxLDL mg/dl
BPF 650 mg twice a day;
*Cynara cardunculus* 100 mg twice a day
Combination 300 mg/single administration
Δ Difference from baseline after 16 week treatment

TABLE 2

| Substances | Dose mg | ALP (u/L) | GGT (U/L) | ALT (u/L) | AST (u/L) | HA (ng/ml) | PCIII (ng/ml) | IVC (ng/ml) | Hep/Index |
|---|---|---|---|---|---|---|---|---|---|
| PLACEBO | | | | | | | | | |
| Baseline | | 65.26 ± 0.7 | 67.44 ± 3.9 | 52 ± 4.1 | 44.5 ± 3.9 | 85.7 ± 10 | 85.7 ± 10 | 85.7 ± 10 | 85.7 ± 10 |
| 16 weeks | | −1.3 ± 0.7 | −2.69 ± 1.1 | −0.35 ± 05 | −046 ± 0.6 | −2.8 ± 3.1 | −1.83 ± 1.5 | −1.57 ± 0.6 | −0.3 ± 01 |
| BPF | | | | | | | | | |
| Baseline | 1300 | 64.61 ± 5.1 | 66.31 ± 4.2 | 59.71 ± 4.1 | 46.58 ± 3.9 | 80.53 ± 8.5 | 71.81 ± 7.5 | 57.62 ± 5.8 | 3.7 ± 0.4 |
| 16 weeks | | 14 ± 1.6 | −16 ± 7.2 | −13.4 ± 2 | 11.30 ± 0.6 | 21 ± 5.2 | −16.4 ± 3.5 | 15.3 ± 3.2 | −12.2 ± 0.3 |
| *CYNARA c.* | | | | | | | | | |
| Baseline | 200 | 62.5 ± 4.9 | 65.6 ± 10 | 59.80 ± 3.9 | 41.6 ± 2.7 | 76.6 ± 9 | 74.9 ± 6.2 | 54.6 ± 6.2 | 127 ± 4 |
| 16 weeks | | −10 ± 1.1 | −12 ± 6.4 | −15 ± 3.1 | 12.3 ± 0.8 | 18 ± 3.2 | −12 ± 2.8 | 10.2 ± 2 | −10.2 ± 0.1 |
| COMB. | | | | | | | | | |
| Baseline | 300 | 64.2 ± 5.1 | 67.38 ± 1.7 | 57.69 ± 2.6 | 45.62 ± 3.1 | 83.67 ± 7.4 | 72.91 ± 6.5 | 58.11 ± 3.9 | 3.9 ± 0.5 |
| 16 weeks | | −18 ± 47 | −18 ± 5.4 | −14 ± 3.6 | 13.2 ± 4.5 | 24.58 ± 6.5 | 18.3 ± 5.8 | 17.6 ± 6 | −12.1 ± 0.2 |

ALP alkaline phosphatase; GGT gamma-glutamyltransferase; ALT alanine aminotransferase; AST aspartate aminotransferase; HA hyaluronic acid; PCIII precollagen IV-c type IV collagen.

The compositions of the invention exhibited a marked activity in lowering total cholesterol, LDLs and blood glucose, as well as increasing cHDL, reducing blood pressure and modulation of inflammatory parameters, and reducing cardiovascular risk factors. The reduction in serum cholesterol, triglycerides and glucose is 38%, 45% and 28% respectively.

The formulations of the invention have also proved effective on different parameters in a range of patients suffering from metabolic syndrome, in whom normalisation of parameters such as blood glucose, lipid parameters, hypertension and "silent inflammation" was observed.

The examples set out below further illustrate the invention.

Example 1—Preparation of *Cynara cardunculus* Var. *Sylvestris* Extract

1000 Kg of freshly-picked *Cynara cardunculus* var. *sylvestris* leaves are finely ground in a grinder under flowing steam to bring the ground biomass to a temperature of about 85° C. in a time compatible with the total enzymatic inhibition of the glycosidases and hydrolases; the biomass is pressed, while still hot, in a screw press, and the aqueous extract is collected, while the squeezed biomass is countercurrent washed with water at 60° C. The combined liquids are clarified by decanter, and the clear solution is absorbed on 20 L of an absorption resin; after washing the resin with water until the non-resin-like substances are completely eliminated, the resin is washed with ethanol and the eluate is concentrated to water.

This solution is cooled and stored until the *Citrus bergamia* extract, obtained by the procedures reported in U.S. Pat. No. 8,741,362, is available.

Example 2—Preparation of Composite Extract of *Citrus bergamia* and *Cynara cardunculus* var. *sylvestris*

5 L of *Cynara cardunculus* var. *sylvestris* extract, prepared according to example 1 and concentrated to 40 brix, was mixed with 12 L of *Citrus bergamia* extract, also concentrated to 40 brix, and the mixture was atomised after filtration.

The resulting extract is a yellow/brown water-soluble powder with a 32% flavonoid content, comprising 4.5% neoeriocitrin, 8.6% naringin, 8.1% neohesperidin and 11.7% cynaropicrin It presents characteristic IR bands at 3347, 2925, 1712.7, 1634.1, 1514.6, 1269.1, 1171.9 and 1021 $cm^{-1}$.

Example 3—Preparation of 300 mg of Hard Gelatin Capsules

Unit Composition:

| | |
|---|---|
| Combination of example 2 | 300 mg |
| Microcrystalline cellulose | 100 mg |
| Silicon dioxide | 5 mg |
| Magnesium stearate | 5 mg |

Example 4—Formulation of the Combination of *Citrus bergamia* Extract and *Cynara cardunculus* Var. *Sylvestris* Extract in Oily Suspension for Soft Gelatin Capsules Unit Composition

| | |
|---|---|
| Combination of example 2 | 300 mg |
| Soya lecithin | 200 mg |
| Beeswax | 5 mg |
| Linseed oil | 225 mg |

The invention claimed is:

1. A composition of matter comprising neoeriocitrin, naringin, neohesperidin and cynaropicrin in relative weight proportions of about 13.5:25.8:24.3:35.1.

2. The composition of matter of claim 1, said composition of matter having a furocoumarin content lower than 400 mg/Kg.

3. The composition of matter of claim 1, said composition of matter substantially free of bergaptene.

4. The composition of matter of claim 1, comprising about 13.5 mg neoeriocitrin, about 25.8 mg naringin, about 24.3 mg neohesperidin, about 35.1 mg cynaropicrin and about 100 mg of pharmaceutically-acceptable excipient, said composition formed into an oral dosage form.

5. The invention of claim 4, wherein said pharmaceutically-acceptable excipient comprises oil rich in omega-3 fatty acid in an amount sufficient to facilitate the absorption of said neoeriocitrin, naringin, neohesperidin or cyanopicrin by the human gastrointestinal system.

6. The composition of matter of claim 1, said composition substantially free of hydrolytic enzymes and oxidants.

7. The composition of matter of claim 1, wherein said neoeriocitrin, naringin, neohesperidin and cynaropicrin have been subject to atomization, wherein said atomization increases the solubility of said neoeriocitrin, naringin, neohesperidin and cynaropicrin.

\* \* \* \* \*